United States Patent
Duggan et al.

(10) Patent No.: US 7,507,836 B2
(45) Date of Patent: Mar. 24, 2009

(54) BENZAMIDE MODULATORS OF METABOTROPIC GLUTAMATE RECEPTORS

(75) Inventors: Mark E. Duggan, Harleysville, PA (US); Craig W. Lindsley, Schwenksville, PA (US); David D. Wisnoski, Lansdale, PA (US)

(73) Assignee: Merck & Co. Inc., Rahway, NJ (US)

( * ) Notice: Subject to any disclaimer, the term of this patent is extended or adjusted under 35 U.S.C. 154(b) by 214 days.

(21) Appl. No.: 10/550,968

(22) PCT Filed: Mar. 22, 2004

(86) PCT No.: PCT/US2004/008627

§ 371 (c)(1),
(2), (4) Date: Sep. 26, 2005

(87) PCT Pub. No.: WO2004/087048

PCT Pub. Date: Oct. 14, 2004

(65) Prior Publication Data

US 2006/0235069 A1  Oct. 19, 2006

Related U.S. Application Data

(60) Provisional application No. 60/457,734, filed on Mar. 26, 2003.

(51) Int. Cl.
C07D 209/48 (2006.01)
C07C 233/05 (2006.01)
A61K 31/40 (2006.01)
A61K 31/165 (2006.01)

(52) U.S. Cl. .................. 548/486; 514/354; 514/417; 514/617; 564/153; 546/323

(58) Field of Classification Search .......... 514/617, 514/417, 354; 564/153; 548/486; 546/323
See application file for complete search history.

(56) References Cited

FOREIGN PATENT DOCUMENTS

WO  WO 00/69816  11/2000
WO  WO 02/46166  6/2002
WO  WO 02/098864  12/2002

OTHER PUBLICATIONS

Chemical Abstracts Service, Columbus Ohio, US; XP002438782, retrieved from STN Accession No. 1962:12809, Database Asscession No. 56:12809, RNs: 93323-83-2 and 98742-49-5.
J. A. O'Brien et al., "A Novel Selective Allosteric Modulator Potentiates the Activity of Native Metabotropic Glutamate Receptor Subtype 5 in Rat Forebain" J. of Pharmacology and Experimental Therapeutics, 2004, vol. 309, No. 2, pp. 568-577.
Database Beilstein, Beilstein Institute for Organic Chemistry, Frankfurt-Main, DE; XP002438783, Database Accession No. BRN:3376420.
Database Beilstein, Beilstein Institute for Organic Chemistry, Frankfurt-Main, DE; XP002438784, Database Accession No. BRN:344532.
Database Beilstein, Beilstein Institute for Organic Chemistry, Frankfurt-Main, DE; XP002438785, Database Accession No. BRN:3461782.
Database Beilstein, Beilstein Institute for Organic Chemistry, Frankfurt-Main, DE; XP002438786, Database Accession No. BRN:2731365.
Database Beilstein, Beilstein Institute for Organic Chemistry, Frankfurt-Main, DE; XP002438787, Database Accession No. BRN:2809287.
Mano, P. De, et al, The constitution of isamic acid, Canadian Journal of Chemistry, 1967, vol. 45, pp. 2177-2190.
Rosevear, J. et al, A comparison of the reactions of some Ethyl N-Arylcarbamates with Those of the Corresponding Acetanilides. II Amidomethylation with N-Hydroxymethylphthalimide, Australian Journal of Chemistry, 1990, vol. 43, No. 2, pp. 339-353.
Beddoes, R. L., et al, Synthesis of 2,3,5,6-Tetrahydro-1H, 4H, 11CH-3a,6a, 11b-Triazbenz(de) Anthracene (5) and X-Ray Crystal Structure Determination of (5), Hexahydro-1H,4H,7H,9bH-3a,6a,9a-Triazaphenalene (1), Benzo(B)-1,5,9-Triazadodecane, N,N',N"-Tritosylamide, and of 1,5,9, Triazadoodecane N,N',N"-Tritosylamide., Tetrahedron, 1987, vol. 43, No. 8, pp. 1903-1920.

*Primary Examiner*—Shailendra Kumar
(74) *Attorney, Agent, or Firm*—J. Eric Thies; William Krovatin

(57) ABSTRACT

The present invention is directed to compounds which are allosteric modulators of metabotropic glutamate receptors, including the mGluR5 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

26 Claims, No Drawings

BENZAMIDE MODULATORS OF METABOTROPIC GLUTAMATE RECEPTORS

CROSS REFERENCE TO RELATED APPLICATIONS

This application is a U.S. National Phase application under 35 U.S.C. §371 of PCT Application No. PCT/US2004/008627, filed Mar. 22, 2004, which claims priority under 35 U.S.C. §119 from U.S. application Ser. No. 60/457,734, filed Mar. 26, 2003.

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to allosteric modulators of mGlu receptors, in particular mGluR5 receptors. The mGluR receptors belong to the Type III G-protein coupled receptor (GPCR) superfamily. This superfamily of GPCR's includes the mGluRs as well as a number of other receptors including the calcium-sensing receptors, GABAB receptors and pheromone receptors. The family III GPCRs are unique in that they are activated by binding of effectors to the amino-terminus portion of the receptor protein. The mGlu receptors are thought to mediate the demonstrated ability of glutamate to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either of glutamate or of other neurotransmitters, or modify the post-synaptic response of neurotransmitters, respectively.

At present, eight distinct mGlu receptors have been positively identified, cloned, and their sequences reported. These are grouped based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGluR receptors, which include the mGluR1 and mGluR5, are known to activate phospholipase C (PLC) via Galphaq-proteins thereby resulting in the increased hydrolysis of phosphoinositides and intracellular calcium mobilization. Aside from the normal agonist glutamate, several compounds have been reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of Galphai-protein. These receptors can be activated by the normal agonist, glutamate, as well as by a selective compound such as 1S,2S,SR,6S-2 aminobicyclo[3.1.0] hexane-2,6-dicarboxylate. Monn, et al., J. Med. Chem., 40, 528 (1997); Schoepp, et al., Neuropharmacol., 36, 1 (1997). Similarly, the Group III mGlu receptors, including mGluR4, mGluR6, mGluR7 and mGluR8, are negatively coupled to adenylate cyclase via Gai and, in addition to the normal agonist, glutamate, are potently activated by L-AP4 (L-(+)-2-amino-4-phosphonobutyric acid). Schoepp, Neurochem. Int., 24, 439 (1994).

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction makes the abatement of these neurological processes an important therapeutic goal.

SUMMARY OF THE INVENTION

The present invention is directed to compounds which are potentiators of metabotropic glutamate receptors, including the mGluR5 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

DETAILED DESCRIPTION OF THE INVENTION

The present invention is directed to compounds of the formula I:

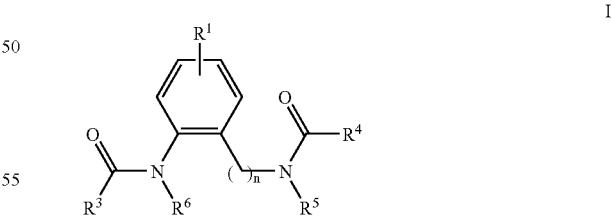

wherein:
$R^1$ is selected from the group consisting of:
(1) hydrogen,
(2) halogen,
(3) $C_{1-6}$alkyl, which is unsubstituted or substituted with halogen, hydroxyl or phenyl,
(4) —$OC_{1-6}$alkyl,
(5) —$S(O)_m$—$C_{1-6}$alkyl, wherein m is selected from 0, 1 and 2, (6) —$CO_2R^9$, wherein $R^9$ is independently selected from:
  (a) hydrogen,
  (b) —$C_{1-6}$alkyl, which is unsubstituted or substituted with 1-6 fluoro,
  (c) benzyl, and
  (d) phenyl,
(7) —$NR^{10}R^{11}$, wherein $R^{10}$ and $R^{11}$ are independently selected from:
  (a) hydrogen,
  (b) —$C_{1-6}$alkyl, which is unsubstituted or substituted with 1-6 fluoro,
  (c) —$C_{5-6}$cycloalkyl,
  (d) benzyl,
  (e) phenyl,
  (f) —$S(O)_2$—$C_{1-6}$alkyl,
  (g) —$S(O)_2$-benzyl, and
  (h) —$S(O)_2$-phenyl,
(8) —$S(O)_2$—$NR^{10}R^{11}$,
(9) phenyl, which is unsubstituted or substituted with one or more substituents independently selected from:
  (a) —$C_{1-6}$alkyl,
  (b) —O—$C_{1-6}$alkyl,
  (c) halo,
  (d) hydroxy,
  (e) trifluoromethyl, and
  (f) —$OCF_3$;
$R^3$ is selected from the group consisting of:
  (1) $C_{1-6}$alkyl, which is unsubstituted or substituted with halogen, hydroxyl or phenyl,
  (2) $C_{3-7}$cycloalkyl, which is unsubstituted or substituted with halogen, hydroxyl or phenyl, and
  (3) phenyl, which is unsubstituted or substituted with one or more substituents independently selected from:
    (a) —$C_{1-6}$alkyl, which is unsubstituted or substituted with —$NR^{10}R^{11}$,
    (b) —O—$C_{1-6}$alkyl,
    (c) halo,
    (d) hydroxy,
    (e) trifluoromethyl,
    (f) —$OCF_3$;
    (g) —$CO_2R^9$,
    (h) —$NR^{10}R^{11}$,
    (i) —$C(O)NR^{10}R^{11}$, and
    (j) —$NO_2$,
  (4) heterocycle, wherein heterocycle is selected from:
    benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, payrolls, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, which is unsubstituted or substituted with one or more substituents independently selected from:
    (a) —$C_{1-6}$alkyl,
    (b) —O—$C_{1-6}$alkyl,
    (c) halo,
    (d) hydroxy,
    (e) phenyl,
    (f) trifluoromethyl,
    (g) —$OCF_3$;
    (h) —$CO_2R^9$,
    (i) —$NR^{10}R^{11}$, and
    (j) —$CONR^{10}R^{11}$;
$R^4$ is selected from the group consisting of:
  (1) $C_{1-6}$alkyl, which is unsubstituted or substituted with halogen, hydroxyl or phenyl,
  (2) $C_{3-7}$cycloalkyl, which is unsubstituted or substituted with halogen, hydroxyl or phenyl, and
  (3) phenyl, which is unsubstituted or substituted with one or more substituents independently selected from:
    (a) —$C_{1-6}$alkyl,
    (b) —O—$C_{1-6}$alkyl,
    (c) halo,
    (d) hydroxy,
    (e) trifluoromethyl,
    (f) —$OCF_3$,
    (g) —$CO_2R^9$,
    (h) —$NR^{10}R^{11}$,
    (i) —$CONR^{10}R^{11}$, and
    (j) —$NO_2$;
  (4) heterocycle, wherein heterocycle is selected from:
    benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, which is unsubstituted or substituted with one or more substituents independently selected from:
    (a) —$C_{1-6}$alkyl,
    (b) —O—$C_{1-6}$alkyl,
    (c) halo,
    (d) hydroxy,
    (e) phenyl,
    (f) trifluoromethyl,
    (g) —$OCF_3$, (h) —CO$_2$R$^9$,
(i) —NR$^{10}$R$^{11}$, and
(j) —CONR$^{10}$R$^{11}$;

or wherein R$^4$ and R$^5$ are joined together to form a phthalimidyl, succinimidyl or glutamidyl ring, which is unsubstituted or substituted with one or more substituents independently selected from the definitions of R$^1$;

R$^5$ and R$^6$ are independently selected from the group consisting of:
(1) hydrogen, and
(2) C$_{1-6}$alkyl;

n is an integer selected from 1, 2 and 3;

and pharmaceutically acceptable salts thereof and individual diastereomers thereof.

An embodiment of the present invention includes compounds of the formula Ia:

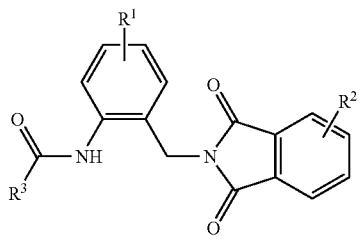

Ia wherein
R$^2$ is selected from the group consisting of:
(1) hydrogen,
(2) —C$_{1-6}$alkyl,
(3) —O—C$_{1-6}$alkyl,
(4) halo,
(5) hydroxy,
(6) —NO$_2$, and
(7) phenyl;

and R$^1$ and R$^3$ are defined herein;

and pharmaceutically acceptable salts thereof and individual enantiomers and diastereomers thereof.

An embodiment of the present invention includes compounds of the formula Ib:

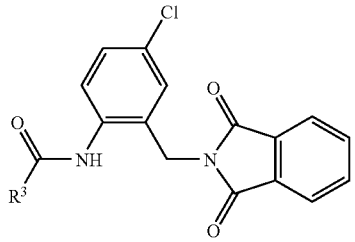

Ib wherein R$^3$ is defined herein;

and pharmaceutically acceptable salts thereof and individual enantiomers and diastereomers thereof.

An embodiment of the present invention includes compounds of the formula Ic:

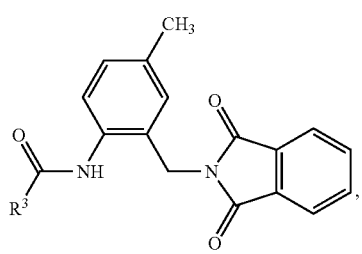

Ic wherein R$^3$ is defined herein;

and pharmaceutically acceptable salts thereof and individual enantiomers and diastereomers thereof.

An embodiment of the present invention includes compounds of the formula Id:

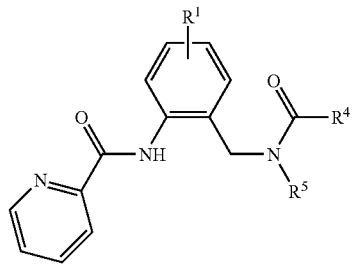

Id wherein R$^1$, R$^2$, R$^4$ and R$^5$ are defined herein;

and pharmaceutically acceptable salts thereof and individual enantiomers and diastereomers thereof.

An embodiment of the present invention includes compounds of the formula Ie:

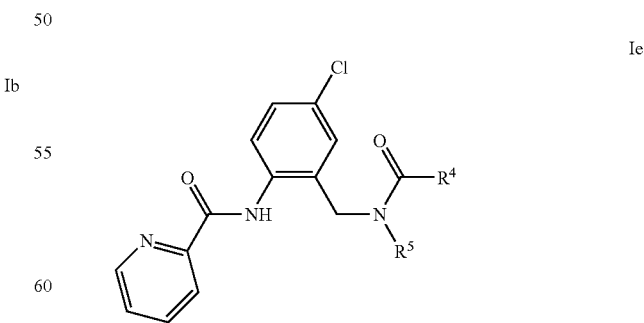

Ie wherein R$^4$ and R$^5$ are defined herein;

and pharmaceutically acceptable salts thereof and individual enantiomers and diastereomers thereof.

An embodiment of the present invention includes compounds of the formula If:

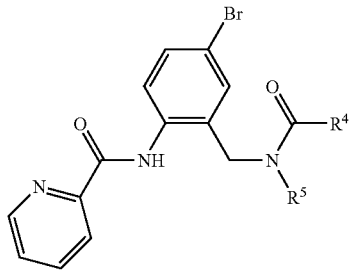

wherein $R^4$ and $R^5$ are defined herein;
and pharmaceutically acceptable salts thereof and individual enantiomers and diastereomers thereof.

An embodiment of the present invention includes compounds wherein $R^1$ is hydrogen.

An embodiment of the present invention includes compounds wherein $R^2$ is halogen.

An embodiment of the present invention includes compounds wherein $R^2$ is fluoro.

An embodiment of the present invention includes compounds wherein $R^2$ is chloro.

An embodiment of the present invention includes compounds wherein $R^2$ is bromo.

An embodiment of the present invention includes compounds wherein $R^2$ is methyl.

An embodiment of the present invention includes compounds wherein $R^3$ is phenyl, which is unsubstituted or substituted with one or more substituents independently selected from:
(a) —$C_{1-6}$alkyl,
(b) —O—$C_{1-6}$alkyl,
(c) halo,
(d) hydroxy,
(e) trifluoromethyl,
(f) —$OCF_3$;
(g) —$CO_2$—$C_{1-6}$alkyl,
(h) —$NH_2$,
(i) —NH—$C_{1-6}$alkyl,
(j) —$CONH_2$, and
(k) —CONH—$C_{1-6}$alkyl.

An embodiment of the present invention includes compounds wherein $R^3$ is phenyl, which is unsubstituted or substituted with hydroxy, halo, —$CONHC_{1-6}$alkyl or —$CO_2C_{1-6}$alkyl.

An embodiment of the present invention includes compounds wherein $R^3$ is pyridyl, pyrimidinyl, pyrazinyl, pyridazinyl, piperazinyl, furanyl or thienyl.

An embodiment of the present invention includes compounds wherein $R^3$ is pyridyl.

An embodiment of the present invention includes compounds wherein $R^3$ is pyrimidinyl.

An embodiment of the present invention includes compounds wherein $R^4$ and $R^5$ are joined together to form a phthalimidyl ring.

An embodiment of the present invention includes compounds wherein $R^5$ is hydrogen or $C_{1-6}$alkyl.

An embodiment of the present invention includes compounds wherein $R^6$ is hydrogen.

An embodiment of the present invention includes compounds wherein n is 1.

Specific embodiments of the present invention include a compound which is selected from the group consisting of the title compounds of the Examples herein and pharmaceutically acceptable salts thereof.

The compounds of the present invention are allosteric modulators of metabotropic glutamate (mGluR) receptor function, in particular they are allosteric modulators of mGluR5 receptors. Allosteric modulation can be positive or negative. Positive allosteric modulators are referred to as "potentiators," and negative allosteric modulators are referred to as "noncompetitive antagonists." The term "potentiator" refers to a compound that increases or augments agonist activity, but which does not itself activate the receptor. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the potentiators of the present invention would be expected to increase the effectiveness of glutamate and glutamate agonists of the mGluR5 receptor. The present noncompetitive antagonists are expected to have their effect at mGluR receptors by virtue of their ability to decrease the response of such receptors to glutamate or glutamate agonists, reducing the function of the receptors. It is recognized that the noncompetitive antagonists of the present invention would be expected to decrease the effectiveness of glutamate and glutamate agonists of the mGluR5 receptor. Thus, the potentiators or noncompetitive antagonists of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic nontoxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylaamine, tripropylamine, tromethaamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of potentiating metabotropic glutamate receptor activity in a patient such as a mammal in need of such potentiation comprising the administration of an effective amount of the compound. The present invention is directed to the use of the compounds disclosed herein as potentiators of metabotropic glutamate receptor activity. In addition to primates, especially humans, a variety of other mammals can be treated according to the method of the present invention.

In a like manner, the subject noncompetitive antagonist compounds are useful in a method of inhibiting metabotropic glutamate receptor activity in a patient such as a mammal in need of such inhibition comprising the administration of an effective amount of the compound. The present invention is directed to the use of the compounds disclosed herein as noncompetitive antagonists of metabotropic glutamate receptor activity. In addition to primates, especially humans, a variety of other mammals can be treated according to the method of the present invention.

The present invention is further directed to a method for the manufacture of a medicament for potentiating or inhibiting metabotropic glutamate receptor activity in humans and animals comprising combining a compound of the present invention with a pharmaceutical carrier or diluent.

The subject treated in the present methods is generally a mammal, preferably a human being, male or female, in whom potentiation or inhibition of metabotorpic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as potentiators or noncompetitive antagonists of metabotropic glutamate receptor activity, in particular mGluR5 activity, may be demonstrated by methodology known in the art. Chinese Hamster Ovary cells transfected with human or rat mGluR5 were plated in clear bottomed assay plates for assay in a Fluorometric Plate Reader (FLIPR). The cells were loaded with a $Ca^{2+}$-sensitive fluorescent dye (e.g. Fluo-4), and the plates were washed and placed in the FLIPR instrument. After establishment of a fluorescence baseline for 10 seconds, the compounds in the present invention were added to the cells, and the response of the cells was measured. Five minutes later, an mGluR5 agonist (e.g, glutamate, 3,5-dihydroxyphenylglycine, or quisqualate) was added to the cells, and the response of the cells was measured. Potentiation of the agonist response of mGluR5 by the compounds in the present invention was observed as an increase in response to non-maximal concentrations of agonist in the presence of compound compared to the response to agonist in the absence of compound. In a like manner, antagonism of the agonist response of mGluR5 by the compounds in the present invention was observed as a decrease in response to non-maximal concentrations of agonist in the presence of compound compared to the response to agonist in the absence of compound.

The assay described above was performed in two modalities. In the first, a range of concentrations of the present compound was added to the cells, followed by a single fixed concentration of agonist. If the compound acted as a potentiator, an $EC_{50}$ value for potentiation and a maximum extent of potentiation by the compound at this concentration of agonist was determined by non-linear curve fitting. If the compound acted as a noncompetitive antagonist, an IC50 value was determined by nonlinear curve fitting. In the second modality, several fixed concentrations of the present compound was added to the various wells on the plate, followed by a range of concentrations of agonist for each concentration of present compound. The $EC_{50}$ values for the agonist at each concentration of compound were determined by non-linear curve fitting. A decrease in the $EC_{50}$ value of the agonist with increasing concentrations of the present compound (a leftward shift of the agonist concentration-response curve) is an indication of the degree of mGluR5 potentiation at a given concentration of the present compound. An increase in the agonist $EC_{50}$ value with increasing concentrations of the present compound (a rightward shift of the agonist concentration-response curve) is an indication of the degree of mGluR5 antagonism at a given concentration of the present compound. This latter modality also demonstrates whether the present compound also affects the maximum response of mGluR5 to agonists.

In particular, the compounds of the following examples had activity in potentiating or inhibiting the mGluR5 receptor in the aforementioned assays, generally with an $EC_{50}$ for potentiation or an $IC_{50}$ for inhibition of less than about 10 μM. Preferred compounds within the present invention had activity in potentiating or inhibiting the mGluR5 receptor in the aforementioned assays with an $EC_{50}$ for potentiation or an $IC_{50}$ for inhibition of less than about 1 μM. Preferred compounds caused a change (increase or decrease) in agonist $EC_{50}$ value of greater than about three-fold. These compounds did not cause mGluR5 to respond in the absence of agonist, and they did not cause a significant increase in the maximal response of the mGluR5 to agonists, although the noncompetitive antagonists did cause a decrease in maximal response to agonists. These compounds acted at potentiators or noncompetitive antagonists of rat mGluR5 as well as human mGluR5. These compounds were selective for mGluR5 compared with other metabotropic glutamate receptors. Such a result is indicative of the intrinsic activity of the compounds in use as potentiators or noncompetitive antagonists of mGluR5 receptor activity.

Metabotropic glutamate receptors including the mGluR5 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Of the disorders above, the treatment of cognitive disorders, anxiety, schizophrenia or psychosis, Parkinson's disease, obesity and addictive behaviors are of particular importance. In a preferred embodiment the present invention provides a method for preventing or treating cognitive disorders, comprising: administering to a patient in need thereof an effective amount of a compound of formula I. In another preferred embodiment the present invention provides a method for preventing or treating anxiety, comprising: administering to a patient in need thereof an effective amount of a compound of formula I. Particularly preferred anxiety disorders are generalized anxiety disorder, panic disorder, and obsessive compulsive disorder. In another preferred embodiment the present invention provides a method for treating schizophrenia or psychosis, comprising: administering to a patient in need thereof an effective amount of a compound of formula I. In another preferred embodiment the present invention provides a method for treating Parkinson's disease, comprising: administering to a patient in need thereof an effective amount of a compound of formula I. In another preferred embodiment the present invention provides a method for preventing or treating obesity, comprising: administering to a patient in need thereof an effective amount of a compound of formula I. In yet another preferred embodiment the present invention provides a method for treating addictive behaviors, comprising: administering to a patient in need thereof an effective amount of a compound of formula I. Particularly preferred addictive behaviors are addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Of the neurological and psychiatric disorders associated with glutamate dysfunction which are treated according to the present invention, the treatment of s cognitive disorders, anxiety, schizophrenia or psychosis, Parkinson's disease, obesity and addictive behaviors are particularly preferred. Particularly preferred anxiety disorders are generalized anxiety disorder, panic disorder, and obsessive compulsive disorder. Particularly preferred addictive behaviors are addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

In another preferred embodiment the present invention provides a method for treating schizophrenia, comprising: administering to a patient in need thereof an effective amount of a compound of formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including schizophrenia and related disorders.

As used herein the term "schizophrenia" includes treatment of those psychotic disorders and related disorders as described in the DSM-IV. The skilled artisan will recognize that there are alternative nomenclatures, nosologies, and classification systems for neurological and psychiatric disorders, and particular schizophrenia, and that these systems-evolve with medical scientific progress. Thus, the term "schizophrenia" is intended to include like disorders that are described in other diagnostic sources.

In another preferred embodiment the present invention provides a method for treating anxiety, comprising: administering to a patient in need thereof an effective amount of a compound of formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

The subject compounds are further useful in a method for the prevention, treatment, control, amelioration, or reducation of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a potentiator compound of the present invention. A potentiated amount is expected to be less than the amount that is required to provided the same effect when the mGluR agonist is administered without an effective amount of a potentiator compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the description of the chemistry and in the Examples that follow are:

| | |
|---|---|
| $CH_2Cl_2$ | dichloromethane |
| DIEA | diisopropylethylamine |
| DMF | N,N-dimethylformamide |
| $CCl_4$ | carbon tetrachloride |
| $Bz_2O_2$ | benzoylperoxide |
| NBS | N-bromosuccinamide |
| PS-DIEA | polystyrene diisopropylethylamine |
| PS-DMAP | polystyrene 4-N,N-dimethylaminopyridine |
| THF | tetrahydrofuran |
| TFA | trifluoroacteic acid |
| MeOH | methanol |
| Ra—Ni | Raney Nickel. |

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove.

Reactions used to generate the compounds of this invention are prepared by employing reactions as shown in the Reaction Schemes I-IV, in addition to other standard manipulations such as ester hydrolysis, cleavage of protecting groups, etc., as may be known in the literature or exemplified in the experimental procedures.

These reactions may be employed in a linear sequence to provide the compounds of the invention or they may be used to synthesize fragments which are subsequently joined by the alkylation reactions described in the Reaction Schemes.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

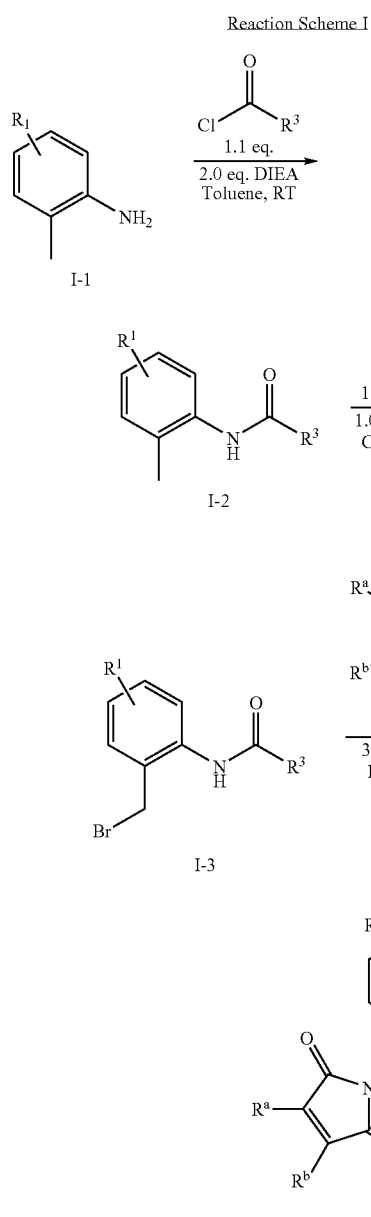

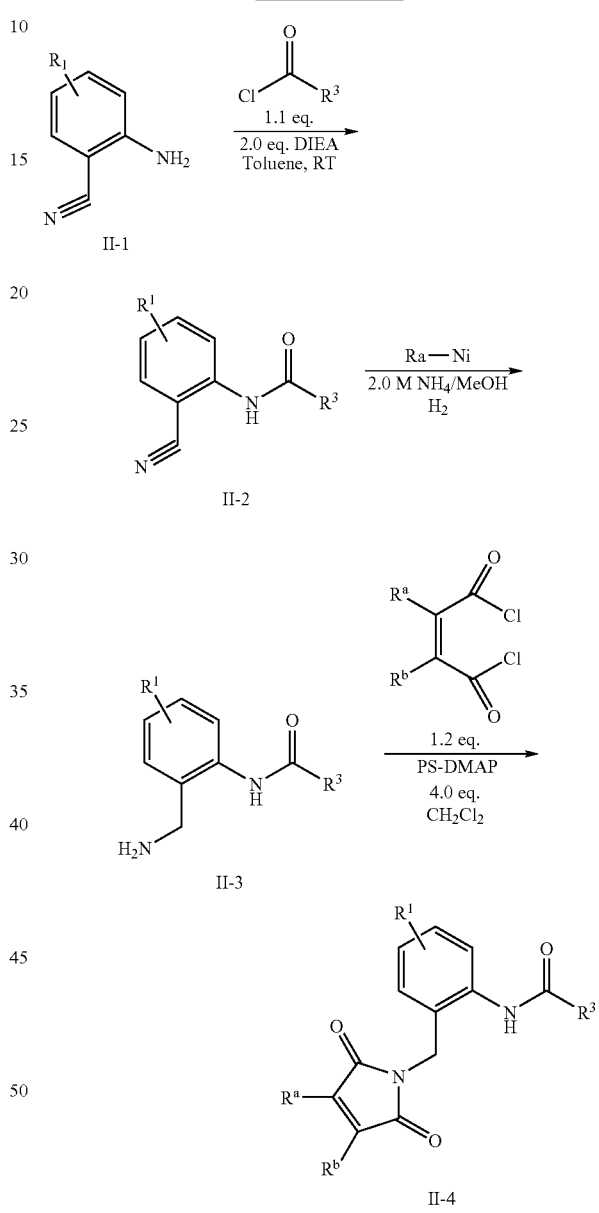

As illustrated in Reaction Scheme I, a suitably substituted othro-methyl aniline I-1 is acylated under standard conditions to provide the corresponding amide I-2. Intermediate I-2 may then be subjected to a standard bromination reaction to deliver benzylic bromide I-3. Intermediate I-3 may then be subjected to nucleophilic displacement of the benzylic bromide with a variety of nitrogen nucleophiles to produce benzamide instant compounds, I-4.

Reaction Scheme II illustrates the preparation of the compounds of this instant invention, starting from a suitably substituted ortho-cyano aniline II-1, that can be acylated under standard conditions to produce II-2. Intermediate II-2 may be reduced by a heterogeneous nickel catalyst under a hydrogen atmosphere to deliver the corresponding benzylic amine II-3. Reaction with a suitably substituted 1,2-diacid halide delivers the corresponding phthalido-benzamide instant compounds, II-4.

Reaction Scheme III

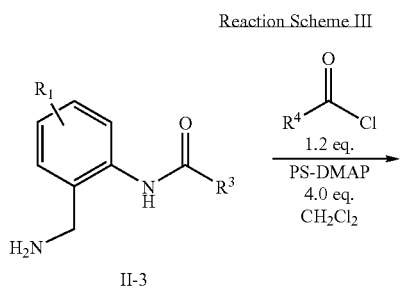

Reaction Scheme III illustrates the preparation of the compounds of this instant invention, starting from intermediate II-3. Acylation under standard conditions provides benzamide instant compounds, III-1.

Reaction Scheme IV

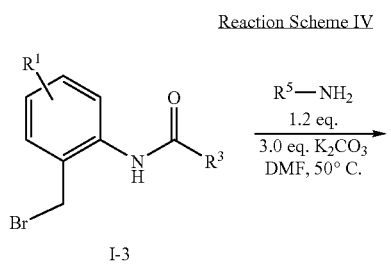

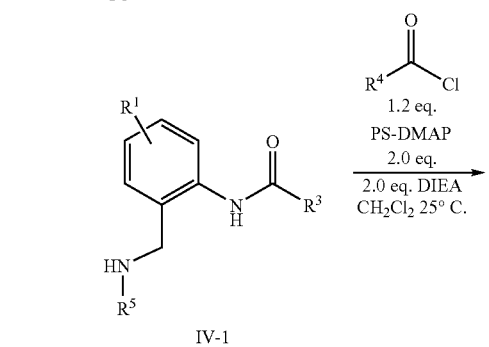

Reaction Scheme IV illustrates the preparation of the compounds of this instant invention, starting from intermediate II-3. Nucleophilic displacement of the benzylic bromide with functionalized primiary amines ($H_2NR^5$) delivers the corresponding benzylic amine IV-1. Acylation under standard conditions provides the benzamide instant compounds, IV-1.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way. Particular materials employed, species and conditions are intended to be further illustrative of the invention and not limitative of the reasonable scope thereof.

SCHEME 1

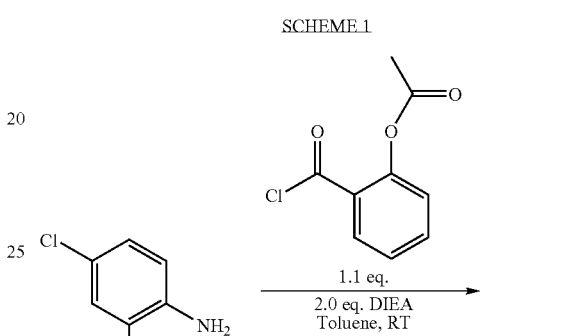

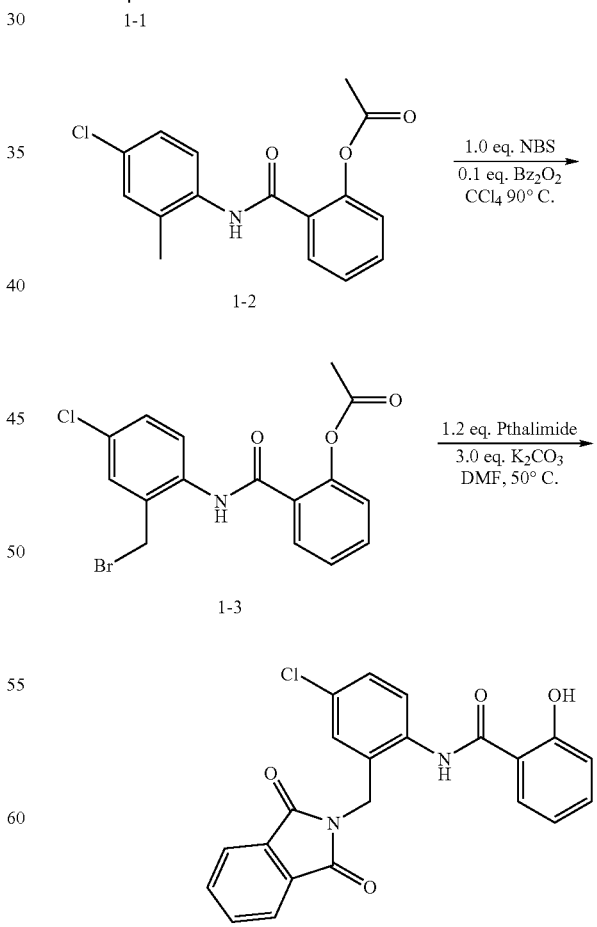

2-{[(4-chloro-2-methylphenyl)amino]carbonyl}phenyl acetate (1-2)

To a stirred solution of 4-chloro-2-methylaniline, 1-1, (10.0 g 0.071 moles) in toluene was added (24.7 mL 0.014 moles) of N,N-diisopropylethylamine, followed by slow addition of acetylsalicyloyl chloride. The mixture was stirred until complete by TLC. Reaction was filtered and dried under vacuum to afford 9.4 grams of 1-2. Analytical LCMS: ($CH_3CN/H_2O$/1% TFA, 4 min gradient), 88% pure, M+1 peak m/e 304.

2-({[2-(bromomethyl)-4-chlorophenyl]amino}carbonyl)phenyl acetate (1-3)

1-2 (9.4 g 0.031 moles) was immediately taken up in a solution of $CCl_4$ with recrystallized N-Bromosuccinimide (5.5 g 0.031 moles) and benzoyl peroxide (0.75 g 3.10 mmoles). The reaction was heated at 90 degrees celsius, along with a light source, until complete by TLC. Upon completion, the solvent was reduced by two-thirds and filtered through a small plug of silica gel yielding 10.5 grams of 1-3. Analytical LCMS: ($CH_3CN/H_2O$/1% TFA, 4 min gradient), 85% pure, M+1 peak m/e 384.

N-{4-chloro-2-[(1,3-dioxo-1,3-dihydro-2H-isoindol-2-yl)methyl]phenyl}-2-hydroxybenzamide (1-4)

Compound 1-3 (6.0 g 0.015 moles) was dissolved in 50 mL of DMF. To that pthalimide (3.31 g 0.023 moles), $K_2CO_3$ (6.2 g 0.045 moles) and a catalytic amount of KI were added and allowed to stir at 50° C. overnight. Upon completion the reaction was diluted with ethyl acetate and then washed with brine (6×25 mL's) to afford 2.9 grams of 1-4 in a crude mixture, which was then purified by normal phase chromatography. $^1$H NMR (300 MHz, $CDCl_3$): 4.83 ppm (2H, S); 7.05 ppm (2H, m); 7.36 ppm (1H, dd, J=2.4 Hz, 8.6 Hz); 7.50 ppm (1H, dt, J=1.5 Hz, 8.5 Hz); 7.59 ppm (1H, d, J=2.4 Hz); 7.75 ppm (3H, m); 7.91 ppm (2H, m); 8.18 ppm (1H, d, 7.2 Hz); 10.17 ppm (1H, s); 12.27 ppm (1H,s) Analytical LCMS: single peak (214 nm) at 3.633 min ($CH_3CN/H_2O$/1% TFA, 4 min gradient), HRMS calc'd for $C_{22}H_{15}N_2O_4Cl$ (M+H), 407.0799; found 407.0793 (M+H).

Compounds in Table 1 were synthesized as shown in Scheme 1, but substituting the appropriately substituted nitrogen nucleophile for phthalimide in Scheme 1, or the appropriatley substituted nitrogen nucleophile or 1,2-diacid chloride in Reaction Schemes 1 and 2. The requisite were commercialy available, described in the literature or readily synthesized by one skilled in the art of organic synthesis.

TABLE 1

| Compound | Nomenclature | MS M + 1 |
| --- | --- | --- |
|  | N-{4-chloro-2-[(1,3-dioxo-1,3-dihydro-2H-isoindol-2-yl)methyl]phenyl}pyridine-2-carboxamide | 392.8 |
|  | N-{4-chloro-2-[(1,3-dioxo-1,3-dihydro-2H-isoindol-2-yl)methyl]phenyl}pyrimidine-2-carboxamide | 393.8 |
|  | N-{4-chloro-2-[(1,3-dioxo-1,3-dihydro-2H-isoindol-2-yl)methyl]phenyl}-2-hydroxybenzamide | 407.8 |

TABLE 1-continued

| Compound | Nomenclature | MS M + 1 |
|---|---|---|
| | 2-[({2-[(1,3-dioxo-1,3-dihydro-2H-isoindol-2-yl)methyl]-3-fluorophenyl}amino)-carbonyl]phenyl acetate | 433.4 |
| | N-{2-[(1,3-dioxo-1,3-dihydro-2H-isoindol-2-yl)methyl]-3-fluorophenyl}-2-hydroxybenzamide | 391.4 |
| | 2-chloro-N-{2-[(1,3-dioxo-1,3-dihydro-2H-isoindol-2-yl)methy]-3-fluorophenyl}benzamide | 409.8 |
| | N-{2-[(1,3-dioxo-1,3-dihydro-2H-isoindol-2-yl)methyl]-3-fluorophenyl}-2-fluorobenzamide | 393.4 |
| | N-{2-[(1,3-dioxo-1,3-dihydro-2H-isoindol-2-yl)methyl]-3-fluorophenyl}benzamide | 375.3 |
| | N-{2-[(1,3-dioxo-1,3-dihydro-2H-isoindol-2-yl)methyl]-3-fluorophenyl}-3,5-difluorobenzamide | 411.3 |

TABLE 1-continued

| Compound | Nomenclature | MS M + 1 |
|---|---|---|
| | N-{2-[(1,3-dioxo-1,3-dihydro-2H-isoindol-2-yl)methyl]-phenyl}pyridine-2-carboxamide | 358.4 |
| | N-{4-chloro-2-[(1,3-dioxo-1,3-dihydro-2H-isoindol-2-yl)methyl]phenyl}-3-methoxybenzamide | 421.8 |
| | N-{4-chloro-2-[(1,3-dioxo-1,3-dihydro-2H-isoindol-2-yl)methyl]phenyl}-2-methylbenzamide | 405.8 |
| | N-{4-chloro-2-[(1,3-dioxo-1,3-dihydro-2H-isoindol-2-yl)methyl]phenyl}-2-furamide | 381.8 |
| | N-{4-chloro-2-[(1,3-dioxo-1,3-dihydro-2H-isoindol-2-yl)methyl]phenyl}-5-methylisoxazole-3-carboxamide | 396.8 |

TABLE 1-continued

| Compound | Nomenclature | MS M + 1 |
|---|---|---|
|  | N-{4-chloro-2-[(1,3-dioxo-1,3-dihydro-2H-isoindol-2-yl)methyl]phenyl}cyclohexanecarboxamide | 397.8 |
|  | N-{5-chloro-2-[(1,3-dioxo-1,3-dihydro-2H-isoindol-2-yl)methyl]phenyl}cyclohexanecarboxamide | 397.8 |
|  | N-{4-chloro-2-[(1,3-dioxo-1,3-dihydro-2H-isoindol-2-yl)methyl]phenyl}-1-methyl-1H-imidazole-2-carboxamide | 395.8 |
|  | N-{4-chloro-2-[(1,3-dioxo-1,3-dihydro-2H-isoindol-2-yl)methyl]phenyl}-1,3-thiazole-4-carboxamide | 398.8 |
|  | N-{4-chloro-2-[(1,3-dioxo-1,3-dihydro-2H-isoindol-2-yl)methyl]phenyl}-3-hydroxypyridine-2-carboxamide | 408.8 |

TABLE 1-continued

| Compound | Nomenclature | MS M + 1 |
|---|---|---|
| | N-{4-chloro-2-[(1,3-dioxo-1,3-dihydro-2H-isoindol-2-yl)methyl]phenyl}imidazo[2,1-b][1,3]thiazole-6-carboxamide | 437.9 |
| | N-{4-chloro-2-[(1,3-dioxo-1,3-dihydro-2H-isoindol-2-yl)methyl]phenyl}-1,2,5-thiadiazole-3-carboxamide | 399.8 |
| | N-{2-[(1,3-dioxo-1,3-dihydro-2H-isoindol-2-yl)methyl]-4-methoxyphenyl}pyridine-2-carboxamide | 388.4 |
| | N-{4-bromo-2-[(4-fluoro-1,3-dioxo-1,3-dihydro-2H-isoindol-2-yl)methyl]-phenyl}pyridine-2-carboxamide | 455.3 |
| | N-{4-chloro-2-[(2,5-dioxo-3-phenyl-2,5-dihydro-1H-pyrrol-1-yl)methyl]-phenyl}pyridine-2-carboxamide | 418.9 |

TABLE 1-continued

| Compound | Nomenclature | MS M + 1 |
|---|---|---|
| | N-{4-chloro-2-[(4-fluoro-1,3-dioxo-1,3-dihydro-2H-isoindol-2-yl)methyl]-phenyl}pyridine-2-carboxamide | 410.8 |
| | N-{4-chloro-2-[(5,6-dimethyl-1,3-dioxo-1,3-dihydro-2H-isoindol-2-yl)methyl]-phenyl}pyridine-2-carboxamide | 420.8 |
| | N-{4-chloro-2-[(5-fluoro-1,3-dioxo-1,3-dihydro-2H-isoindol-2-yl)methyl]-phenyl}pyridine-2-carboxamide | 410.8 |
| | N-{4-chloro-2-[(5-ethoxy-1,3-dioxo-1,3-dihydro-2H-isoindol-2-yl)methyl]-phenyl}pyridine-2-carboxamide | 436.9 |

TABLE 1-continued

| Compound | Nomenclature | MS M + 1 |
|---|---|---|
| | N-{5-bromo-3-[(5,6-dichloro-1,3-dioxo-1,3-dihydro-2H-isoindol-2-yl)methyl]pyridin-2-yl}pyridine-2-carboxamide | 507.1 |
| | N-{4-chloro-2-[(5-hydroxy-1,3-dioxo-1,3-dihydro-2H-isoindol-2-yl)methyl]-phenyl}pyridine-2-carboxamide | 408.8 |
| | N-{4-bromo-2-[(5-fluoro-1,3-dioxo-1,3-dihydro-2H-isoindol-2-yl)methyl]-phenyl}pyridine-2-carboxamide | 455.2 |
| | N-{4-bromo-2-[(5-ethoxy-1,3-dioxo-1,3-dihydro-2H-isoindol-2-yl)methyl]-phenyl}pyridine-2-carboxamide | 481.3 |
| | N-{4-bromo-2-[(5,6-dichloro-1,3-dioxo-1,3-dihydro-2H-isoindol-2-yl)methyl]-phenyl}pyridine-2-carboxamide | 506.1 |

TABLE 1-continued

| Compound | Nomenclature | MS M + 1 |
|---|---|---|
| | N-{4-bromo-2-[(4,6-dichloro-1,3-dioxo-1,3-dihydro-2H-isoindol-2-yl)methyl]-phenyl}pyridine-2-carboxamide | 506.1 |
| | N-{2-[(4,6-dichloro-1,3-dioxo-1,3-dihydro-2H-isoindol-2-yl)methyl]-4-fluorophenyl}pyridine-2-carboxamide | 445.2 |
| | N-{2-[(5,6-dichloro-1,3-dioxo-1,3-dihydro-2H-isoindol-2-yl)methyl]-4-fluorophenyl}pyridine-2-carboxamide | 445.2 |
| | N-{4-fluoro-2-[(5-nitro-1,3-dioxo-1,3-dihydro-2H-isoindol-2-yl)methyl]-phenyl}pyridine-2-carboxamide | 421.4 |
| | N-{4-bromo-2-[(4-methyl-1,3-dioxo-3,4,5,6-tetrahydrocyclopenta[c]pyrrol-2(1H)-yl)methyl]-phenyl}pyridine-2-carboxamide | 441.3 |

SCHEME 2

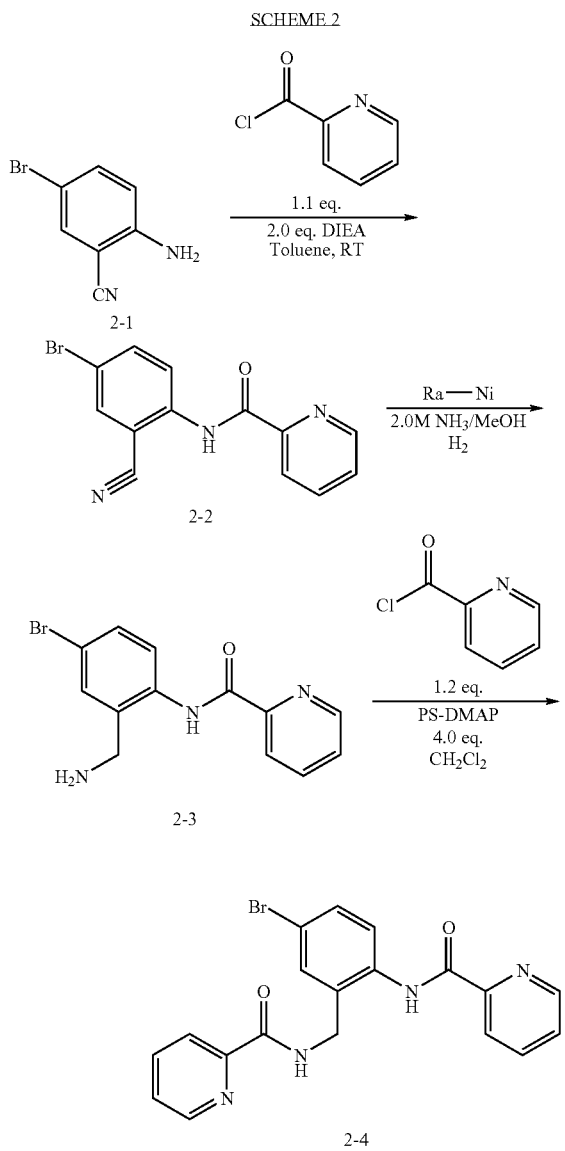

N-(4-bromo-2-cyanophenyl)pyridine-2-carboxamide (2-2)

To a stirred solution of 2-amino-5-bromobenzonitrile 2-1 (2.8 g, 0.014 moles) in toluene was added (4.95 mL, 0.028 moles) of N,N-diisopropylethylamine, followed by slow addition of (2.74 g, 0.015 moles) picolinoyl chloride. The mixture was stirred until complete by TLC. Reaction was filtered and dried under vacuum to afford 3 grams of 2-2. Analytical LCMS: ($CH_3CN/H_2O$/1% TFA, 4 min gradient), 95% pure, M+1 peak m/e 301.

N-[2-(aminomethyl)-4-bromophenyl]pyridine-2-carboxamide (2-3)

2-2 (3 g, 0.0099 moles) was immediately taken up in a solution of 2.0M ammonia in methanol. To this solution was added catalytic Raney nickel. The reaction was stirred with a hydrogen balloon attached until complete by TLC. Upon completion, the reaction was filtered and the solvent was removed yielding 2.9 grams of 2-3. Analytical LCMS: ($CH_3CN/H_2O$/1% TFA, 4 min gradient), 95% pure, M+1 peak m/e 306.

N-{5-bromo-2-[(pyridin-2-ylcarbonyl)amino]benzyl}pyridine-2-carboxamide (2-4)

Compound 2-3 (0.050 g, 0.16 mmoles) was dissolved in 6 mL of methylene chloride. To the reaction vessel was added (0.06 mL, 0.32 mmoles) of N,N-diisopropylethylamine and (200 mg, 0.32 mmols, 1.49 mmol/gram) followed by the addition of (0.057 g, 0.32 mmol) picolinoyl chloride. The mixture was stirred until complete by TLC. The compound was then filtered and then the solvent was removed and then purified on a mass guided LC/MS to provide 46 mg (70%) of the title compound. $^1$H NMR (300 MHz, $CDCl_3$): 8.89 ppm (s, 2H), 8.43 ppm (m, 2H), 8.22 ppm (m, 2H), 8.13 ppm (t, J=4 Hz, 1H), 8.0 ppm (s, 1H), 7.81 ppm (m, 2H), 7.41 ppm (m, 1H), 7.2 ppm (m, 2H), 4.22 ppm (d, J=4 Hz, 2H); HRMS calc'd for $C_{19}H_{15}BrN_4O_2$ (M+1) 411.0451; Found: 411.0444

Compounds in Table 2 were synthesized as shown in Scheme 2, but substituting the appropriately substituted acid chloride for picolinoyl chloride in Scheme 2, or the appropriatley substituted acid chloride in Reaction Scheme 3 or by the appropriatley substituted primary amine ($R^7NH_2$) and acid chloride in Reaction Scheme 4. The requisite were commercialy available, described in the literature or readily synthesized by one skilled in the art of organic synthesis.

TABLE 2

| Compound | Nomenclature | MS M + 1 |
|---|---|---|
|  | N-(4-bromo-2-{[(2-fluorobenzoyl)amino]methyl}phenyl)pyridine-2-carboxamide | 429.3 |

TABLE 2-continued

| Compound | Nomenclature | MS M + 1 |
|---|---|---|
| | N-{5-bromo-2-[(pyridin-2-ylcarbonyl)amino]-benzyl}pyridine-2-carboxamide | 412.3 |
| | N-[4-bromo-2-({[2-(trifluoromethyl)benzoyl]-amino}methyl)-phenyl]pyridine-2-carboxamide | 479.3 |
| | N-(4-chloro-2-{[(3,5-dichlorobenzoyl)(ethyl)-amino]methyl}phenyl)-pyridine-2-carboxamide | 463.8 |
| | N-(2-{[(4-butoxybenzoyl)(ethyl)-amino]methyl}-4-chlorophenyl)pyridine-2-carboxamide | 467 |

TABLE 2-continued

| Compound | Nomenclature | MS M + 1 |
|---|---|---|
| | N-(4-chloro-2-{[(3,5-dimethoxybenzoyl)(ethyl)-amino]methyl}phenyl)-pyridine-2-carboxamide | 454.9 |
| | N-(4-chloro-2-{[(3,4-dichlorobenzoyl)(ethyl)-amino]methyl}phenyl)-pyridine-2-carboxamide | 463.8 |
| | N-(4-chloro-2-{[(3,5-dichlorobenzoyl)(isobutyl)-amino]methyl}phenyl)-pyridine-2-carboxamide | 491.8 |
| | N-(4-chloro-2-{[(3,5-dimethoxybenzoyl)-(isobutyl)amino]methyl}-phenyl)pyridine-2-carboxamide | 483 |

TABLE 2-continued

| Compound | Nomenclature | MS M + 1 |
|---|---|---|
| | N-{5-fluoro-2-[(pyridin-2-ylcarbonyl)amino]-benzyl}quinoxaline-2-carboxamide | 402.4 |
| | N-(2-{[(4-butoxybenzoyl)amino]-methyl}-4-fluorophenyl)pyridine-2-carboxamide | 422.5 |
| | N-(4-bromo-2-{[(3-methoxybenzoyl)-(methyl)amino]methyl}-phenyl)pyridine-2-carboxamide | 455.3 |
| | N-(4-chloro-2-{[(3,5-dichlorobenzoyl)-(methyl)amino]methyl}-phenyl)pyridine-2-carboxamide | 449.7 |

TABLE 2-continued

| Compound | Nomenclature | MS M + 1 |
|---|---|---|
| | N-(2-{[[3,5-bis(trifluoromethyl)benzoyl](methyl)amino]methyl}-4-chlorophenyl)pyridine-2-carboxamide | 516.8 |
| | N-[4-chloro-2-({(3,5-dichlorobenzoyl)[2-(dimethylamino)ethyl]amino}methyl)phenyl]-pyridine-2-carboxamide | 506.8 |
| | N-[2-(benzoylamino)-5-bromobenzyl]-N,3,5-trimethylbenzamide | 452.4 |
| | N-(4-bromo-2-{[(3,5-dichlorobenzoyl)-(methyl)amino]methyl}-phenyl)pyridine-2-carboxamide | 494.2 |

TABLE 2-continued

| Compound | Nomenclature | MS M + 1 |
|---|---|---|
| | N-(4-bromo-2-{[(3,4-difluorobenzoyl)-(methyl)amino]methyl}-phenyl)pyridine-2-carboxamide | 461.3 |
| | N-(4-bromo-2-{[(2,4-difluorobenzoyl)-(methyl)amino]methyl}-phenyl)pyridine-2-carboxamide | 461.3 |
| | N-(4-bromo-2-{[(3,4-dichlorobenzoyl)-(methyl)amino]methyl}-phenyl)pyridine-2-carboxamide | 494.2 |
| | N-[4-chloro-2-({methyl[2-(trifluoromethyl)-benzoyl]amino}methyl)-phenyl]pyridine-2-carboxamide | 448.2 |
| | N-(4-chloro-2-{[(3,4-dichlorobenzoyl)-(methyl)amino]methyl}-phenyl)pyridine-2-carboxamide | 449.7 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above.

What is claimed is:
1. A compound of the formula I:

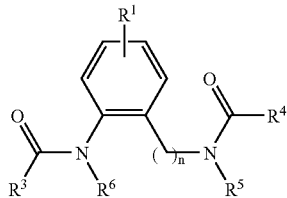

wherein:
R$^1$ is selected from the group consisting of:
(1) hydrogen,
(2) halogen,
(3) C$_{1-6}$alkyl, which is unsubstituted or substituted with halogen, hydroxyl or phenyl,
(4) —OC$_{1-6}$alkyl,
(5) —S(O)$_m$—C$_{1-6}$alkyl, wherein m is selected from 0, 1 and 2,
(6) —CO$_2$R$^9$, wherein R$^9$ is independently selected from:
  (a) hydrogen,
  (b) —C$_{1-6}$alkyl, which is unsubstituted or substituted with 1-6 fluoro,
  (c) benzyl, and
  (d) phenyl,
(7) —NR$^{10}$R$^{11}$, wherein R$^{10}$ and R$^{11}$ are independently selected from:
  (a) hydrogen,
  (b) —C$_{1-6}$alkyl, which is unsubstituted or substituted with 1-6 fluoro,
  (c) —C$_{5-6}$cycloalkyl,
  (d) benzyl,
  (e) phenyl,
  (f) —S(O)$_2$—C$_{1-6}$alkyl,
  (g) —S(O)$_2$-benzyl, and
  (h) —S(O)$_2$-phenyl,
(8) —S(O)$_2$—NR$^{10}$R$^{11}$,
(9) phenyl, which is unsubstituted or substituted with one or more substituents independently selected from:
  (a) —C$_{1-6}$alkyl,
  (b) —O—C$_{1-6}$alkyl,
  (c) halo,
  (d) hydroxy,
  (e) trifluoromethyl, and
  (f) —OCF$_3$;
R$^3$ is selected from the group consisting of:
(1) C$_{1-6}$alkyl, which is substituted with halogen, hydroxyl or phenyl,
(2) C$_{3-7}$cycloalkyl, which is unsubstituted or substituted with halogen, hydroxyl or phenyl, and
(3) phenyl, which is unsubstituted or substituted with one or more substituents independently selected from:
  (a) —C$_{1-6}$alkyl, which is unsubstituted or substituted with —NR$^{10}$R$^{11}$,
  (b) —O—C$_{1-6}$alkyl,
  (c) halo,
  (d) hydroxy,
  (e) trifluoromethyl,
  (f) —OCF$_3$;
  (g) —CO$_2$R$^9$,
  (h) —NR$^{10}$R$^{11}$,
  (i) —C(O)NR$^{10}$R$^{11}$, and
  (j) —NO$_2$,
(4) heterocycle, wherein heterocycle is selected from:
  benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, which is unsubstituted or substituted with one or more substituents independently selected from:
  (a) —C$_{1-6}$alkyl,
  (b) —O—C$_{1-6}$alkyl,
  (c) halo,
  (d) hydroxy,
  (e) phenyl,
  (f) trifluoromethyl,
  (g) —OCF$_3$;
  (h) —CO$_2$R$^9$,
  (i) —NR$^{10}$R$^{11}$, and
  (j) —CONR$^{10}$R$^{11}$;
R$^4$ is selected from the group consisting of:
(1) C$_{1-6}$alkyl, which is unsubstituted or substituted with halogen, hydroxyl or phenyl,
(2) C$_{3-7}$cycloalkyl, which is unsubstituted or substituted with halogen, hydroxyl or phenyl, and
(3) phenyl, which is unsubstituted or substituted with one or more substituents independently selected from:
  (a) —C$_{1-6}$alkyl,
  (b) —O—C$_{1-6}$alkyl,
  (c) halo,
  (d) hydroxy,
  (e) trifluoromethyl,
  (f) —OCF$_3$,
  (g) —CO$_2$R$^9$,
  (h) —NR$^{10}$R$^{11}$,
  (i) —CONR$^{10}$R$^{11}$, and
  (j) —NO$_2$;
(4) heterocycle, wherein heterocycle is selected from:
  benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof, which is unsubstituted or substituted with one or more substituents independently selected from:
- (a) —$C_{1-6}$alkyl,
- (b) —O—$C_{1-6}$alkyl,
- (c) halo,
- (d) hydroxy,
- (e) phenyl,
- (f) trifluoromethyl,
- (g) —$OCF_3$,
- (h) —$CO_2R^9$,
- (i) —$NR^{10}R^{11}$, and
- (j) —$CONR^{10}R^{11}$;

or wherein $R^4$ and $R^5$ are joined together to form a phthalimidyl, succinimidyl or glutamidyl ring, which is unsubstituted or substituted with one or more substituents independently selected from the definitions of $R^2$;

$R^2$ is selected from the group consisting of:
- (1) hydrogen,
- (2) —$C_{1-6}$alkyl,
- (3) —O—$C_{1-6}$alkyl,
- (4) halo,
- (5) hydroxyl,
- (6) —$NO_2$, and
- (7) phenyl;

$R^5$ and $R^6$ are independently selected from the group consisting of:
- (1) hydrogen, and
- (2) $C_{1-6}$alkyl;

n is an integer selected from 1, 2 and 3;

with the proviso that the compound of formula I is not:
- N-[4-chloro-2-[(1,3-dihydro- 1,3-dioxo-2H-isoindol-2-yl)methyl]phenyl]-acetamide,
- N-[2-[(1,3-dihydro- 1,3-dioxo-2H-isoindol-2-yl)methyl]-4-methylphenyl]-acetamide, or
- N-[2-[(1,3-dihydro- 1,3-dioxo-2H-isoindol-2-yl)methyl]phenyl]-acetamide;

or a pharmaceutically acceptable salt thereof.

2. The compound of claim 1 of the formula Ia:

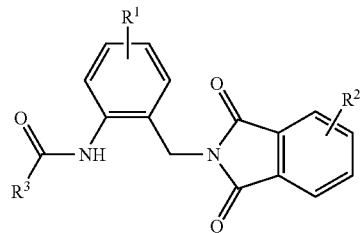

wherein
$R^2$ is selected from the group consisting of:
- (1) hydrogen,
- (2) —$C_{1-6}$alkyl,
- (3) —O—$C_{1-6}$alkyl,
- (4) halo,
- (5) hydroxy,
- (6) —$NO_2$, and
- (7) phenyl;

or a pharmaceutically acceptable salt thereof.

3. The compound of claim 1 of the formula Ib:

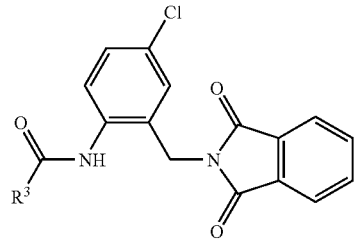

or a pharmaceutically acceptable salt thereof.

4. The compound of claim 1 of the formula Ic:

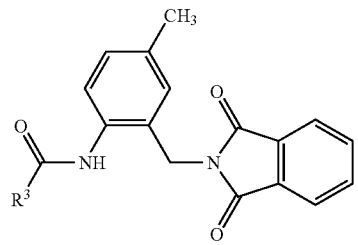

or a pharmaceutically acceptable salt thereof.

5. The compound of claim 1 of the formula Id:

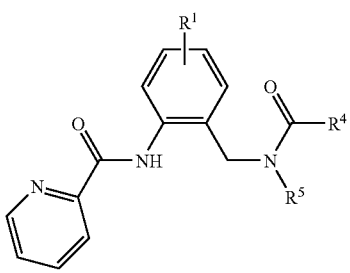

or a pharmaceutically acceptable salt thereof.

6. The compound of claim 1 of the formula Ie:

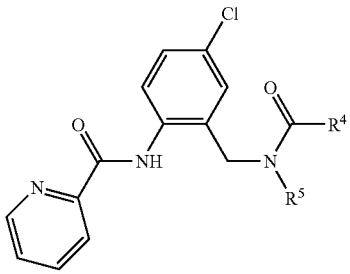

or a pharmaceutically acceptable salt thereof.

7. The compound of claim 1 of the formula If:

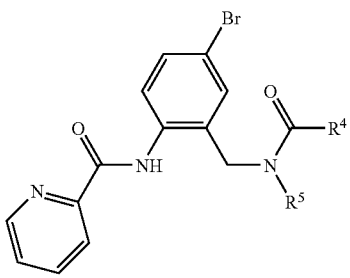

or a pharmaceutically acceptable salt thereof.

8. The compound of claim 1 wherein $R^1$ is hydrogen.
9. The compound of claim 1 wherein $R^2$ is halo.
10. The compound of claim 9 wherein $R^2$ is fluoro.
11. The compound of claim 9 wherein $R^2$ is chloro.
12. The compound of claim 9 wherein $R^2$ is bromo.
13. The compound of claim 1 wherein $R^2$ is methyl.
14. The compound of claim 1 wherein $R^3$ is phenyl, which is unsubstituted or substituted with one or more substituents independently selected from:
   (a) —$C_{1-6}$alkyl,
   (b) —O—$C_{1-6}$alkyl,
   (c) halo,
   (d) hydroxy,
   (e) trifluoromethyl,
   (f) —$OCF_3$;
   (g) —$CO_2$—$C_{1-6}$alkyl,
   (h) —$NH_2$,
   (i) —NH—$C_{1-6}$alkyl,
   (j) —$CONH_2$, and
   (k) —CONH—$C_{1-6}$alkyl.

15. The compound of claim 14 wherein $R^3$ is phenyl, which is unsubstituted or substituted with hydroxy, halo, —$CONHC_{1-6}$alkyl or —$CO_2C_{1-6}$alkyl.

16. The compound of claim 1 wherein $R^3$ is pyridyl, pyrimidinyl, pyrazinyl, pyridazinyl, piperazinyl, furanyl or thienyl.

17. The compound of claim 1 wherein $R^4$ and $R^5$ are joined together to form a phthalimidyl ring.

18. The compound of claim 1 wherein $R^5$ is hydrogen or $C_{1-6}$alkyl.

19. The compound of claim 1 wherein $R^6$ is hydrogen.

20. The compound of claim 1 wherein n is 1.

21. A compound which is selected from the group consisting of:

N-{4-chloro-2-[(1,3-dioxo-1,3-dihydro-2H-isoindol-2-yl)methyl]phenyl}-2-hydroxybenzamide;

N-{4-chloro-2-[(1,3-dioxo-1,3-dihydro-2H-isoindol-2-yl)methyl]phenyl}pyridine-2-carboxamide;

N-{4-chloro-2-[(1,3-dioxo-1,3-dihydro-2H-isoindol-2-yl)methyl]phenyl}pyrimidine-2-carboxamide;

N-{4-chloro-2-[(1,3-dioxo-1,3-dihydro-2H-isoindol-2-yl)methyl]phenyl}-2-hydroxybenzamide;

2-[({2-[(1,3-dioxo-1,3-dihydro-2H-isoindol-2-yl)methyl]-3-fluorophenyl}amino)carbonyl]phenyl;

N-{2-[(1,3-dioxo-1,3-dihydro-2H-isoindol-2-yl)methyl]-3-fluorophenyl}-2-hydroxybenzamide;

2-chloro-N-{2-[(1,3-dioxo-1,3-dihydro-2H-isoindol-2-yl)methyl]-3-fluorophenyl}benzamide;

N-{2-[(1,3-dioxo-1,3-dihydro-2H-isoindol-2-yl)methyl]-3-fluorophenyl}-2-fluorobenzamide;

N-{2-[(1,3-dioxo-1,3-dihydro-2H-isoindol-2-yl)methyl]-3-fluorophenyl}benzamide;

N-{2-[(1,3-dioxo-1,3-dihydro-2H-isoindol-2-yl)methyl]-3-fluorophenyl}-3,5-difluorobenzamide;

N-{2-[(1,3-dioxo-1,3-dihydro-2H-isoindol-2-yl)methyl]phenyl}pyridine-2-carboxamide;

N-{4-chloro-2-[(1,3-dioxo-1,3-dihydro-2H-isoindol-2-yl)methyl]phenyl}-3-methoxybenzamide;

N-{4-chloro-2-[(1,3-dioxo-1,3-dihydro-2H-isoindol-2-yl)methyl]phenyl}-2-methylbenzamide;

N-{4-chloro-2-[(1,3-dioxo-1,3-dihydro-2H-isoindol-2-yl)methyl]phenyl}-2-furamide;

N-{4-chloro-2-[(1,3-dioxo-1,3-dihydro-2H-isoindol-2-yl)methyl]phenyl}-5-methylisoxazole-3-carboxamide;

N-{4-chloro-2-[(1,3-dioxo-1,3-dihydro-2H-isoindol-2-yl)methyl]phenyl}cyclohexanecarboxamide;

N-{5-chloro-2-[(1,3-dioxo-1,3-dihydro-2H-isoindol-2-yl)methyl]phenyl}cyclohexanecarboxamide;

N-{4-chloro-2-[(1,3-dioxo-1,3-dihydro-2H-isoindol-2-yl)methyl]phenyl}-1-methyl-1H-imidazole-2-carboxamide;

N-{4-chloro-2-[(1,3-dioxo-1,3-dihydro-2H-isoindol-2-yl)methyl]phenyl}-1,3-thiazole-4-carboxamide;

N-{4-chloro-2-[(1,3-dioxo-1,3-dihydro-2H-isoindol-2-yl)methyl]phenyl}-3-hydroxypyridine-2-carboxamide;

N-{4-chloro-2-[(1,3-dioxo-1,3-dihydro-2H-isoindol-2-yl)methyl]phenyl}imidazo[2,1-b][1,3]thiazole-6-carboxamide;

N-{4-chloro-2-[(1,3-dioxo-1,3-dihydro-2H-isoindol-2-yl)methyl]phenyl}-1,2,5-thiadiazole-3-carboxamide;

N-{2-[(1,3-dioxo-1,3-dihydro-2H-isoindol-2-yl)methyl]-4-methoxyphenyl}pyridine-2-carboxamide;

N-{4-bromo-2-[(4-fluoro-1,3-dioxo-1,3-dihydro-2H-isoindol-2-yl)methyl]phenyl}pyridine-2-carboxamide;

N-{4-chloro-2-[(2,5-dioxo-3-phenyl-2,5-dihydro-1H-pyrrol-1-yl)methyl]phenyl}pyridine-2-carboxamide;
N-{4-chloro-2-[(4-fluoro-1,3-dioxo-1,3-dihydro-2H-isoindol-2-yl)methyl]phenyl}pyridine-2-carboxamide;
N-{4-chloro-2-[(5,6-dimethyl-1,3-dioxo-1,3-dihydro-2H-isoindol-2-yl)methyl]phenyl}pyridine-2-carboxamide;
N-{4-chloro-2-[(5-fluoro-1,3-dioxo-1,3-dihydro-2H-isoindol-2-yl)methyl]phenyl}pyridine-2-carboxamide;
N-{4-chloro-2-[(5-ethoxy-1,3-dioxo-1,3-dihydro-2H-isoindol-2-yl)methyl]phenyl}pyridine-2-carboxamide;
N-{5-bromo-3-[(5,6-dichloro-1,3-dioxo-1,3-dihydro-2H-isoindol-2-yl)methyl]pyridin-2-yl}pyridine-2-carboxamide;
N-{4-chloro-2-[(5-hydroxy-1,3-dioxo-1,3-dihydro-2H-isoindol-2-yl)methyl]phenyl}pyridine-2-carboxamide;
N-{4-bromo-2-[(5-fluoro-1,3-dioxo-1,3-dihydro-2H-isoindol-2-yl)methyl]phenyl}pyridine-2-carboxamide;
N-{4-bromo-2-[(5-ethoxy-1,3-dioxo-1,3-dihydro-2H-isoindol-2-yl)methyl]phenyl}pyridine-2-carboxamide;
N-{4-bromo-2-[(5,6-dichloro-1,3-dioxo-1,3-dihydro-2H-isoindol-2-yl)methyl]phenyl}pyridine-2-carboxamide;
N-{4-bromo-2-[(4,6-dichloro-1,3-dioxo-1,3-dihydro-2H-isoindol-2-yl)methyl]phenyl}pyridine-2-carboxamide;
N-{2-[(4,6-dichloro-1,3-dioxo-1,3-dihydro-2H-isoindol-2-yl)methyl]-4-fluorophenyl}pyridine-2-carboxamide;
N-{2-[(5,6-dichloro-1,3-dioxo-1,3-dihydro-2H-isoindol-2-yl)methyl]-4-fluorophenyl}pyridine-2-carboxamide;
N-{4-fluoro-2-[(5-nitro-1,3-dioxo-1,3-dihydro-2H-isoindol-2-yl)methyl]phenyl}pyridine-2-carboxamide;
N-{4-bromo-2-[(4-methyl-1,3-dioxo-3,4,5,6-tetrahydrocyclopenta[c]-pyrrol-2(1H)-yl)methyl]phenyl}pyridine-2-carboxamide;
N-{5-bromo-2-[(pyridin-2-ylcarbonyl)amino]benzyl}pyridine-2-carboxamide;
N-(4-bromo-2-{[(2-fluorobenzoyl)amino]methyl}phenyl)pyridine-2-carboxamide;
N-{5-bromo-2-[(pyridin-2-ylcarbonyl)amino]benzyl}pyridine-2-carboxamide;
N-[4-bromo-2-({[2-(trifluoromethyl)benzoyl]amino}methyl)phenyl]-pyridine-2-carboxamide;
N-(4-chloro-2-{[(3,5-dichlorobenzoyl)(ethyl)amino]methyl}phenyl)-pyridine-2-carboxamide;
N-(2-{[(4-butoxybenzoyl)(ethyl)amino]methyl}-4-chlorophenyl)-pyridine-2-carboxamide;
N-(4-chloro-2-{[(3,5-dimethoxybenzoyl)(ethyl)amino]methyl}phenyl)pyridine-2-carboxamide;
N-(4-chloro-2-{[(3,4-dichlorobenzoyl)(ethyl)amino]methyl}phenyl)pyridine-2-carboxamide;
N-(4-chloro-2-{[(3,5-dichlorobenzoyl)(isobutyl)amino]methyl}phenyl)pyridine-2-carboxamide;
N-(4-chloro-2-{[(3,5-dimethoxybenzoyl)(isobutyl)amino]methyl}phenyl)pyridine-2-carboxamide;
N-{5-fluoro-2-[(pyridin-2-ylcarbonyl)amino]benzyl}quinoxaline-2-carboxamide;
N-(2-{[(4-butoxybenzoyl)amino]methyl}-4-fluorophenyl)pyridine-2-carboxamide;
N-(4-bromo-2-{[(3-methoxybenzoyl)(methyl)amino]methyl}phenyl)pyridine-2-carboxamide;
N-(4-chloro-2-{[(3,5-dichlorobenzoyl)(methyl)amino]methyl}phenyl)pyridine-2-carboxamide;
N-(2-{[[3,5-bis(trifluoromethyl)benzoyl](methyl)amino]methyl}-4-chlorophenyl)pyridine-2-carboxamide;
N-[4-chloro-2-({(3,5-dichlorobenzoyl) [2-(dimethylamino)ethyl]amino}methyl)-phenyl]pyridine-2-carboxamide;
N-[2-(benzoylamino)-5-bromobenzyl]-N,3,5-trimethylbenzamide;
N-(4-bromo-2-{[(3,5-dichlorobenzoyl)(methyl)amino]methyl}-phenyl)pyridine-2-carboxamide;
N-(4-bromo-2-{[(3,4-difluorobenzoyl)(methyl)amino]methyl}phenyl)-pyridine-2-carboxamide;
N-(4-bromo-2-{[(2,4-difluorobenzoyl)(methyl)amino]methyl}phenyl)-pyridine-2-carboxamide;
N-(4-bromo-2-{[(3,4-dichlorobenzoyl)(methyl)amino]methyl}phenyl)-pyridine-2-carboxamide;
N-[4-chloro-2-({methyl[2-(trifluoromethyl)benzoyl]amino}methyl)-phenyl]pyridine-2-carboxamide;
N-(4-chloro-2-{[(3,4-dichlorobenzoyl)(methyl)amino]methyl}-phenyl)pyridine-2-carboxamide;
or a pharmaceutically acceptable salt thereof.

22. A compound which is:

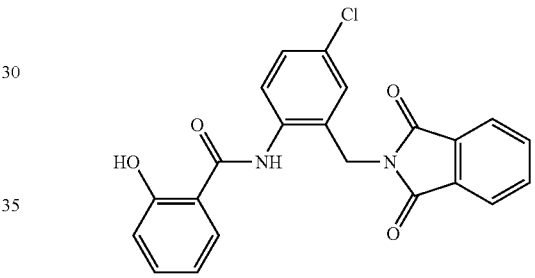

or a pharmaceutically acceptable salt thereof.

23. A pharmaceutical composition which comprises an insert carrier and a compound of claim 1 or a pharmaceutically acceptable salt thereof.

24. A pharmaceutical composition which comprises an inert carrier and a compound of claim 21 or a pharmaceutically acceptable salt thereof.

25. A method for potentiation or inhibition of metabotropic glutamate receptor activity in a mammal which comprises the administration of an effective amount of the compound of claim 1 or a pharmaceutically acceptable salt thereof.

26. A method for treating, controlling, or reducing the risk of schizophrenia in a mammalian patient in need of such which comprises administering to the patient a therapeutically effective amount of the compound of claim 1 or a pharmaceutically acceptable salt thereof.

* * * * *